United States Patent
Tang (10) Patent No.: US 10,563,878 B2
(45) Date of Patent: Feb. 18, 2020

(54) CONTROLLING TEMPERATURE REGULATING DEVICE BASED ON USER'S INTERNAL BODY TEMPERATURE AND SKIN TEMPERATURE RECEIVED FROM WEARABLE DEVICES

(71) Applicant: Huawei Technologies Co., Ltd., Shenzhen (CN)

(72) Inventor: Weidong Tang, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 368 days.

(21) Appl. No.: 15/408,576

(22) Filed: Jan. 18, 2017

(65) Prior Publication Data

US 2017/0122615 A1 May 4, 2017

Related U.S. Application Data

(63) Continuation of application No. PCT/CN2015/086860, filed on Aug. 13, 2015.

(30) Foreign Application Priority Data

Aug. 15, 2014 (CN) .......................... 2014 1 0405123

(51) Int. Cl.
*F24F 120/10* (2018.01)
*F24F 11/30* (2018.01)
(Continued)

(52) U.S. Cl.
CPC ............ *F24F 11/30* (2018.01); *A61B 5/0008* (2013.01); *A61B 5/01* (2013.01); *A61B 5/681* (2013.01);
(Continued)

(58) Field of Classification Search
CPC .......... F24F 11/30; A61B 5/01; A61B 5/0008; A61B 2560/0228; A61B 5/6826;
(Continued)

(56) References Cited

U.S. PATENT DOCUMENTS 3,744,555 A * 7/1973 Fletcher ............. G05D 23/1931
165/46
4,475,158 A * 10/1984 Elias .................. A61B 10/0012
600/549

(Continued)

FOREIGN PATENT DOCUMENTS

| CN | 1936444 A | 3/2007 |
| CN | 201514001 U | 6/2010 |

(Continued)

OTHER PUBLICATIONS

Machine Translation and Abstract of Chinese Publication No. CN1936444, Mar. 28, 2007, 10 pages.

(Continued)

*Primary Examiner* — Robert E Fennema
*Assistant Examiner* — Marzia T Monty
(74) *Attorney, Agent, or Firm* — Conley Rose, P.C.

(57) ABSTRACT

A control for a temperature regulating device which adjusts the temperature according to the body temperature of the user and control parameters of the temperature regulating device.

13 Claims, 3 Drawing Sheets

(51) Int. Cl.
*A61B 5/00* (2006.01)
*A61B 5/01* (2006.01)
*F24F 110/00* (2018.01)
*F24F 120/14* (2018.01)
*F24F 11/56* (2018.01)

(52) U.S. Cl.
CPC ............ *A61B 5/682* (2013.01); *A61B 5/6815* (2013.01); *A61B 5/6821* (2013.01); *A61B 5/6824* (2013.01); *A61B 5/6826* (2013.01); *A61B 2560/0228* (2013.01); *F24F 11/56* (2018.01); *F24F 2110/00* (2018.01); *F24F 2120/10* (2018.01); *F24F 2120/14* (2018.01)

(58) Field of Classification Search
CPC ..... A61B 5/6824; A61B 5/6821; A61B 5/682; A61B 5/681; A61B 5/6815
See application file for complete search history.

(56) References Cited

U.S. PATENT DOCUMENTS

| | | | | |
|---|---|---|---|---|
| 6,120,460 | A * | 9/2000 | Abreu | A61B 3/1241 600/405 |
| 7,813,840 | B2 | 10/2010 | Suyama et al. | |
| 8,606,374 | B2 | 12/2013 | Fadell et al. | |
| 2008/0077044 | A1* | 3/2008 | Nakayama | A61B 5/01 600/549 |
| 2008/0262381 | A1* | 10/2008 | Kolen | A61B 5/0008 600/549 |
| 2009/0221888 | A1 | 9/2009 | Wijesiriwardana | |
| 2012/0065783 | A1 | 3/2012 | Fadell et al. | |
| 2013/0315069 | A1 | 11/2013 | Douglas et al. | |
| 2014/0073486 | A1 | 3/2014 | Ahmed et al. | |
| 2014/0207292 | A1* | 7/2014 | Ramagem | G05B 15/02 700/278 |

FOREIGN PATENT DOCUMENTS

| | | | |
|---|---|---|---|
| CN | 101916126 | A | 12/2010 |
| CN | 102679492 | A | 9/2012 |
| CN | 103592975 | A | 2/2014 |
| CN | 203704244 | U | 7/2014 |
| CN | 104236016 | A | 12/2014 |
| EP | 1740089 | B1 | 10/2011 |
| JP | 5747144 | A | 3/1982 |
| JP | 2004225930 | A | 8/2004 |
| JP | 2009092282 | A | 4/2009 |
| KR | 20120065661 | A | 6/2012 |

OTHER PUBLICATIONS

Machine Translation and Abstract of Chinese Publication No. CN101916126, Dec. 15, 2010, 7 pages.
Machine Translation and Abstract of Chinese Publication No. CN102679492, Sep. 19, 2012, 12 pages.
Machine Translation and Abstract of Chinese Publication No. CN103592975, Feb. 19, 2014, 10 pages.
Machine Translation and Abstract of Chinese Publication No. CN104236016, Dec. 24, 2014, 10 pages.
Machine Translation and Abstract of Chinese Publication No. CN201514001, Jun. 23, 2010, 6 pages.
Machine Translation and Abstract of Chinese Publication No. CN203704244, Jul. 9, 2014, 5 pages.
Machine Translation and Abstract of Japanese Publication No. JP57047144, Mar. 17, 1982, 10 pages.
Machine Translation and Abstract of Japanese Publication No. JP2004225930, Aug. 12, 2004, 8 pages.
Machine Translation and Abstract of Japanese Publication No. JP2009092282, Apr. 30, 2009, 17 pages.
Machine Translation and Abstract of Korean Publication No. KR20120065661, Jun. 21, 2012, 26 pages.
Foreign Communication From a Counterpart Application, Chinese Application No. 201410405123.3, Chinese Office Action dated Jun. 2, 2016, 9 pages.
Foreign Communication From a Counterpart Application, PCT Application No. PCT/CN2015/086860, English Translation of International Search Report dated Nov. 19, 2015, 3 pages.
Foreign Communication From a Counterpart Application, PCT Application No. PCT/CN2015/086860, English Translation of Written Opinion dated Nov. 19, 2015, 6 pages.
Foreign Communication From a Counterpart Application, European Application No. 15831512.7, Extended European Search Report dated Jun. 23, 2017, 8 pages.

* cited by examiner

ND SKIN TEMPERATURE RECEIVED FROM
WEARABLE DEVICES

CROSS-REFERENCE TO RELATED APPLICATIONS

This application is a continuation of International Application No. PCT/CN2015/086860 filed on Aug. 13, 2015, which claims priority to Chinese Patent Application No. 201410405123.3 filed on Aug. 15, 2014. The disclosures of the aforementioned applications are hereby incorporated by reference in their entireties.

TECHNICAL FIELD

The present disclosure relates to the field of electronic technologies, and in particular, to a method and an apparatus for controlling a temperature regulating device, and a wearable device.

BACKGROUND

With improvement of living standards, now air conditioners are installed in most of residences. An air conditioner is controlled to regulate an indoor temperature, so as to provide a user with a better and more comfortable indoor environment.

At present, when a user needs to regulate a temperature by using an air conditioner, the user may set a specified temperature on the air conditioner by using a matching air-conditioner remote control of the air conditioner. The air conditioner performs cooling or heating according to an indoor temperature and the specific temperature, so that the indoor temperature is kept around the specific temperature.

In a process of implementing the present disclosure, the inventor finds that the approach has at least the following problem.

A user needs to use an air-conditioner remote control to set a specific temperature on an air conditioner, and it is possible that the user sometimes is unwilling to adjust the air conditioner by himself/herself, and keeps the air conditioner running in a current state even though an indoor condition is uncomfortable. This cannot provide the user with a comfortable indoor environment, and moreover, wastes energy.

SUMMARY

To resolve a problem in the prior art, the present disclosure provides a method and an apparatus for controlling a temperature regulating device, and a wearable device. The technical solutions are as follows.

According to a first aspect, an embodiment of the present disclosure provides a method for controlling a temperature regulating device, where the method includes receiving a body temperature of a user sent by a wearable device, where the body temperature of the user includes at least an in vivo temperature of the user; obtaining a control parameter of the temperature regulating device according to the body temperature of the user; and controlling the temperature regulating device according to the control parameter.

With reference to the first aspect, in a first possible implementation manner of the first aspect, the obtaining a control parameter of the temperature regulating device according to the body temperature of the user includes determining, according to the in vivo temperature of the user, a first temperature range including the in vivo temperature of the user; and obtaining the control parameter of the temperature regulating device from a correspondence between an in vivo temperature range and a control parameter according to the first temperature range.

With reference to the first aspect, in a second possible implementation manner of the first aspect, the body of the user further includes a skin temperature of the user, the wearable device includes a first wearable device and a second wearable device, the first wearable device is configured to measure the in vivo temperature of the user, and the second wearable device is configured to measure the skin temperature of the user; and the receiving a body temperature of a user sent by a wearable device includes receiving the in vivo temperature of the user sent by the first wearable device, and receiving the skin temperature of the user sent by the second wearable device.

With reference to the second possible implementation manner of the first aspect, in a third possible implementation manner of the first aspect, the obtaining a control parameter of the temperature regulating device according to the body temperature of the user includes determining, according to the in vivo temperature of the user, a first temperature range including the in vivo temperature of the user; determining, according to the skin temperature of the user, a second temperature range including the skin temperature of the user; and obtaining the control parameter of the temperature regulating device from a correspondence among an in vivo temperature range, a skin temperature range and a control parameter according to the first temperature range and the second temperature range.

With reference to the second possible implementation manner of the first aspect, in a fourth possible implementation manner of the first aspect, the obtaining a control parameter of the temperature regulating device according to the body temperature of the user includes calculating a temperature parameter of the user according to the in vivo temperature and the skin temperature of the user; determining, according to the temperature parameter of the user, a third temperature range including the temperature parameter of the user; and obtaining the control parameter of the temperature regulating device from a correspondence between a temperature parameter range and a control parameter according to the third temperature range.

With reference to the fourth possible implementation manner of the first aspect, in a fifth possible implementation manner of the first aspect, the calculating a temperature parameter of the user according to the in vivo temperature and the skin temperature of the user includes obtaining a first weight corresponding to the in vivo temperature and a second weight corresponding to the skin temperature; and calculating the temperature parameter of the user according to the in vivo temperature of the user and the first weight, and the skin temperature of the user and the second weight.

With reference to the first aspect, in a sixth possible implementation manner of the first aspect, the controlling the temperature regulating device according to the control parameter includes sending the control parameter to the temperature regulating device, so that the temperature regulating device adjusts a temperature according to the control parameter.

According to a second aspect, an embodiment of the present disclosure provides a wearable device, where the wearable device includes a body, a wireless communications module, and a temperature collection module, and the wireless communications module and the temperature collection module are attached on the body; the body is inside a body of a user or is attached on a skin surface of the user; the temperature collection module is configured to collect an in vivo temperature or a skin temperature of the user; and the wireless communications module is configured to send the in vivo temperature or skin temperature of the user to a control center.

With reference to the second aspect, in a first possible implementation manner of the second aspect, the temperature collection module is a temperature sensor.

With reference to the second aspect, in a second possible implementation manner of the second aspect, the wearable device further includes a determining module, where the determining module is configured to determine whether the in vivo temperature of the user falls within a first preset range, and record the in vivo temperature of the user if the in vivo temperature of the user falls within the first preset range, or mark the in vivo temperature of the user as an invalid temperature if the in vivo temperature of the user does not fall within the first preset range; or the determining module is configured to determine whether the skin temperature of the user falls within a second preset range, record the skin temperature of the user if the skin temperature of the user falls within the second preset range, or mark the skin temperature of the user as an invalid temperature if the skin temperature of the user does not fall within the second preset range.

According to a third aspect, an embodiment of the present disclosure provides an apparatus for controlling a temperature regulating device, where the apparatus includes a receiving module, configured to receive a body temperature of a user sent by a wearable device, where the body temperature of the user includes at least an in vivo temperature of the user; an obtaining module, configured to obtain a control parameter of the temperature regulating device according to the body temperature of the user; and a control module, configured to control the temperature regulating device according to the control parameter.

With reference to the third aspect, in a first possible implementation manner of the third aspect, the obtaining module includes a first determining unit, configured to determine, according to the in vivo temperature of the user, a first temperature range including the in vivo temperature of the user; and a first obtaining unit, configured to obtain the control parameter of the temperature regulating device from a correspondence between an in vivo temperature range and a control parameter according to the first temperature range.

With reference to the third aspect, in a second possible implementation manner of the third aspect, the body of the user further includes a skin temperature of the user, the wearable device includes a first wearable device and a second wearable device, the first wearable device is configured to measure the in vivo temperature of the user, and the second wearable device is configured to measure the skin temperature of the user; and the receiving module is configured to receive the in vivo temperature of the user sent by the first wearable device, and receive the skin temperature of the user sent by the second wearable device.

With reference to the second possible implementation manner of the third aspect, in a third possible implementation manner of the third aspect, the obtaining module includes a second determining unit, configured to determine, according to the in vivo temperature of the user, a first temperature range including the in vivo temperature of the user; a third determining unit, configured to determine, according to the skin temperature of the user, a second temperature range including the skin temperature of the user; and a second obtaining unit, configured to obtain the control parameter of the temperature regulating device from a correspondence among an in vivo temperature range, a skin temperature range and a control parameter according to the first temperature range and the second temperature range.

With reference to the second possible implementation manner of the third aspect, in a fourth possible implementation manner of the third aspect, the obtaining module includes a calculation unit, configured to calculate a temperature parameter of the user according to the in vivo temperature and the skin temperature of the user; a fourth determining unit, configured to determine, according to the temperature parameter of the user, a third temperature range including the temperature parameter of the user; and a third obtaining unit, configured to obtain the control parameter of the temperature regulating device from a correspondence between a temperature parameter range and a control parameter according to the third temperature range.

With reference to the fourth possible implementation manner of the third aspect, in a fifth possible implementation manner of the third aspect, the calculation unit includes an obtaining subunit, configured to obtain a first weight corresponding to the in vivo temperature and a second weight corresponding to the skin temperature; and a calculation subunit, configured to calculate the temperature parameter of the user according to the in vivo temperature of the user and the first weight, and the skin temperature of the user and the second weight.

With reference to the third aspect, in a sixth possible implementation manner of the third aspect, the control module is configured to send the control parameter to the temperature regulating device, so that the temperature regulating device adjusts a temperature according to the control parameter.

According to a fourth aspect, the present disclosure provides an apparatus for controlling a temperature regulating device, where the apparatus includes a memory and a processor, configured to execute the method for controlling a temperature regulating device according to the first aspect.

In embodiments of the present disclosure, a control center receives a body temperature of a user sent by a wearable device, obtains a control parameter of a temperature regulating device according to the body temperature of the user, and controls the temperature regulating device according to the control parameter. This not only can provide the user with a comfortable indoor environment, but also can improve energy utilization.

BRIEF DESCRIPTION OF DRAWINGS

To describe the technical solutions in the embodiments of the present disclosure more clearly, the following briefly describes the accompanying drawings required for describing the embodiments. The accompanying drawings in the following description show merely some embodiments of the present disclosure, and a person of ordinary skill in the art may still derive other drawings from these accompanying drawings without creative efforts.

DESCRIPTION OF EMBODIMENTS

To make the objectives, technical solutions, and advantages of the present disclosure clearer, the following further describes the embodiments of the present disclosure in detail with reference to the accompanying drawings.

Embodiment 1

Figure 1:
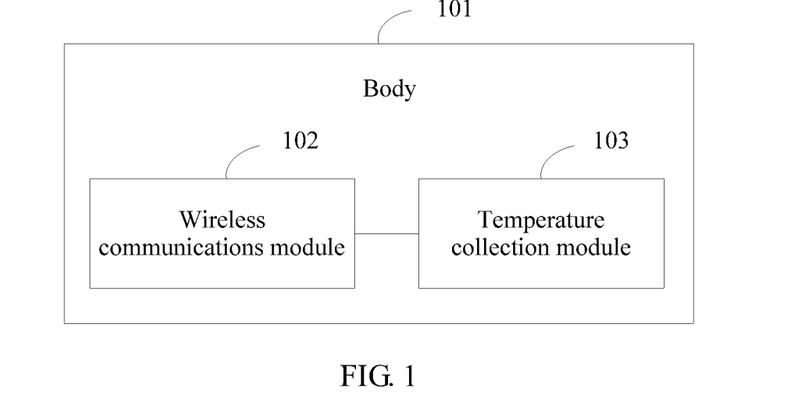
FIG. 1 is a schematic structural diagram of a wearable device according to Embodiment 1 of the present disclosure.

This embodiment of the present disclosure provides a wearable device. Referring to FIG. 1, the wearable device includes a body 101, a wireless communications module 102, and a temperature collection module 103, and the wireless communications module 102 and the temperature collection module 103 are attached on the body 101.

The body 101 is inside a body of a user or is attached on a skin surface of the user; the temperature collection module 103 is configured to collect an in vivo temperature or a skin temperature of the user; and the wireless communications module 102 is configured to send the in vivo temperature or skin temperature of the user to a control center.

In this embodiment of the present disclosure, the wearable device includes a first wearable device and a second wearable device. The first wearable device is inside the body of the user and is configured to measure the in vivo temperature of the user. The first wearable device may be an earphone, a tooth, and contact lenses that have a temperature collection module and a wireless communications module, and the earphone, tooth, or contact lenses are inside the body of the user. Therefore, the temperature collection module in the earphone, tooth, or contact lenses can collect the in vivo temperature of the user.

The second wearable device is attached on the skin surface of the user, and is configured to measure the skin temperature of the user. The second wearable device may be a watch, a ring, or the like that has a temperature collection module and a wireless communications module. The watch and the ring are attached on the skin surface of the user. Therefore, the temperature collection module in the watch or ring can collect the skin temperature of the user.

The temperature collection module 103 may be a temperature sensor or the like.

The user wears the wearable device, and the wearable device measures the in vivo temperature of the user or skin of the user every a preset time. If the user just wears or removes the wearable device, a body temperature that is of the user and that is collected by the temperature collection module in the wearable device may experience an increasing or decreasing process, which probably takes 20 to 30 seconds to be stable. An in vivo temperature or a skin temperature that is of the user and that is undergoing a phase during which a collected in vivo temperature or skin temperature of the user is increasing or decreasing is not an actual in vivo temperature of the user.

Preferably, the wearable device further includes a determining module.

The determining module is configured to determine whether the in vivo temperature of the user falls within a first preset range, and record the in vivo temperature of the user if the in vivo temperature of the user falls within the first preset range, or mark the in vivo temperature of the user as an invalid temperature if the in vivo temperature of the user does not fall within the first preset range. Alternatively, the determining module is configured to determine whether the skin temperature of the user falls within a second preset range, and record the skin temperature of the user if the skin temperature of the user falls within the second preset range, or mark the skin temperature of the user as an invalid temperature if the skin temperature of the user does not fall within the second preset range.

If one control center is set within one range, the control center within the range first obtains a location of the wearable device, and determines, according to the location of the wearable device, whether the wearable device falls within the range.

Preferably, the wearable device further includes a positioning module.

The positioning module is configured to obtain a current location.

In this embodiment of the present disclosure, a wearable device includes a body, a wireless communications module, and a temperature collection module. The wireless communications module and the temperature collection module are attached on the body, and the body is inside a body of a user or is attached on a skin surface of the user; the temperature collection module collects an in vivo temperature or a skin temperature of the user; and the wireless communications module sends the in vivo temperature or skin temperature of the user to a control center, so that the control center obtains a control parameter of a temperature regulating device according to the in vivo temperature or skin temperature of the user, and controls the temperature regulating device according to the control parameter. This not only can provide the user with a comfortable indoor environment, but also can improve energy utilization.

Embodiment 2

Figure 2:
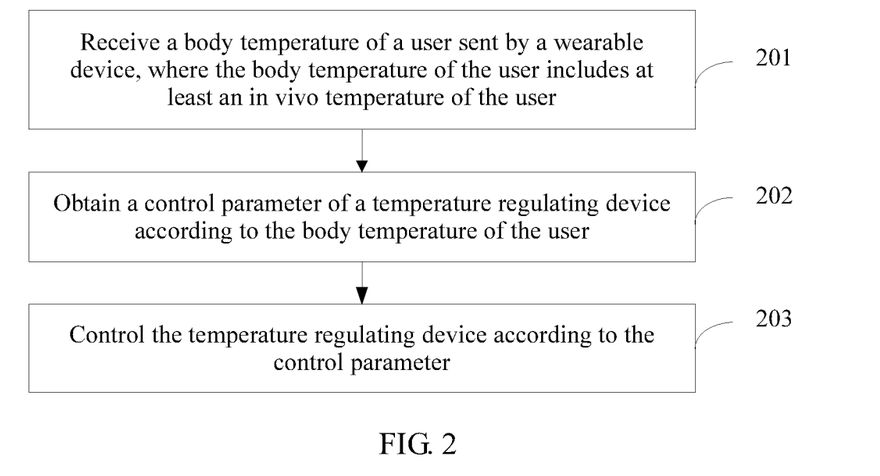
FIG. 2 is a flowchart of a method for controlling a temperature regulating device according to Embodiment 2 of the present disclosure.

This embodiment of the present disclosure provides a method for controlling a temperature regulating device. Referring to FIG. 2, the method includes:

Step 201: Receive a body temperature of a user sent by a wearable device, where the body temperature of the user includes at least an in vivo temperature of the user.

Step 202: Obtain a control parameter of the temperature regulating device according to the body temperature of the user.

Step 203: Control the temperature regulating device according to the control parameter.

In this embodiment of the present disclosure, a control center receives a body temperature of a user sent by a wearable device, obtains a control parameter of a temperature regulating device according to the body temperature of the user, and controls the temperature regulating device according to the control parameter. This not only can provide the user with a comfortable indoor environment, but also can improve energy utilization.

Embodiment 3

Figure 3:
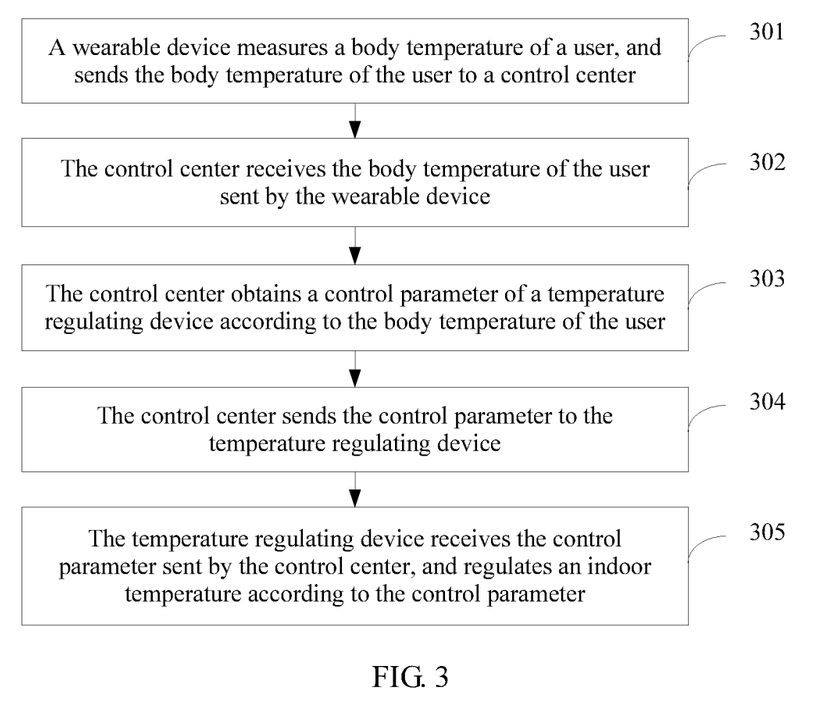
FIG. 3 is a flowchart of a method for controlling a temperature regulating device according to Embodiment 3 of the present disclosure.

This embodiment of the present disclosure provides a method for controlling a temperature regulating device. Referring to FIG. 3, the method includes the following steps.

Step 301: A wearable device measures a body temperature of a user, and sends the body temperature of the user to a control center.

The body temperature of the user includes at least an in vivo temperature of the user; and the body temperature of the user may further include a skin temperature of the user, or the like.

The wearable device includes a first wearable device and a second wearable device; the first wearable device is inside a body of the user, and is configured to measure the in vivo temperature of the user; and the second wearable device is attached on a skin surface of the user, and is configured to measure the skin temperature of the user.

The first wearable device may be an earphone, a tooth, contact lenses, or the like that has a temperature collection module and a wireless communications module, and the earphone may be a wired earphone or a wireless earphone. The second wearable device may be a watch, a ring, or the like that has a temperature collection module and a wireless communications module.

The user wears the first wearable device, and the first wearable device measures the in vivo temperature of the user every a first preset time. If the user just wears or removes the first wearable device, an in vivo temperature that is of the user and that is collected by the temperature collection module in the first wearable device may experience an increasing or decreasing process, which probably takes 20 to 30 seconds to be stable. An in vivo temperature that is of the user and that is undergoing a phase during which a collected in vivo temperature of the user is increasing or decreasing is not an actual in vivo temperature of the user. Therefore, the first wearable device determines a collected in vivo temperature of the user by using the following step, so as to determine whether the collected in vivo temperature of the user is available.

The first wearable device determines whether the in vivo temperature of the user falls within a first preset range, and records the in vivo temperature of the user if the in vivo temperature of the user falls within the first preset range, or marks the in vivo temperature of the user as an invalid temperature if the in vivo temperature of the user does not fall within the first preset range.

The first preset time may be set or changed according to a demand, for example, the first preset time is 10 seconds; and the first preset range may be set or changed according to the in vivo temperature of the user, for example, the first preset range is 35.9° C. to 37.1° C.

For example, the first wearable device measures the in vivo temperature of the user every 10 seconds, and in vivo temperatures that are of the user and that are from the first period to the ninth period are respectively 20° C., 30° C., 35.9° C., 36.0° C., 36.0° C., 36.0° C., 36.0° C., 29.9° C., and 28.8° C. If the first preset range is 35.9° C. to 37.1° C., then the first wearable device determines that 35.9° C., 36.0° C., 36.0° C., 36.0° C., and 36.0° C. are within the range of 35.9° C. to 37.1° C., and records 35.9° C., 36.0° C., 36.0° C., 36.0° C., and 36.0° C.; and the first wearable device determines that 20° C., 30° C., 29.9° C., and 28.8° C. are outside the range of 35.9° C. to 37.1° C., and sets 20° C., 30° C., 29.9° C., and 28.8° C. as invalid temperatures.

Similarly, the user wears the second wearable device, and the second wearable device measures the skin temperature of the user every a second preset time. If the user just wears or removes the second wearable device, a skin temperature that is of the user and that is collected by the temperature collection module in the second wearable device may experience an increasing or decreasing process, which probably takes 20 to 30 seconds to be stable. A skin temperature that is of the user and that is undergoing a phase during which a collected skin temperature of the user is increasing or decreasing is not an actual skin temperature of the user. Therefore, the second wearable device determines a collected skin temperature of the user by using the following step, so as to determine whether the collected skin temperature of the user is available.

The second wearable device determines whether the skin temperature of the user falls within a second preset range, and records the skin temperature of the user if the skin temperature of the user falls within the second preset range, or marks the skin temperature of the user as an invalid temperature if the skin temperature of the user does not fall within the second preset range.

The second preset time may be set or changed according to a demand, for example, the second preset time is 5 seconds; and a second preset range may be set or changed according to the skin temperature of the user, for example, the second preset range is 33° C. to 35° C.

For example, the second wearable device measures the skin temperature of the user every 5 seconds, and skin temperatures that are of the user and that are from the first period to the sixteenth period are respectively 32° C., 33.9° C., 34° C., 34° C., 34° C., 34° C., 34° C., 34° C., 34° C., 34° C., 34° C., 33.5° C., 30° C., 29° C., 25° C., and 12° C. The second wearable devices determines that 33.9° C., 34° C., 34° C., 34° C., 34° C., 34° C., 34° C., 34° C., 34° C., and 33.5° C. are within the range of 33° C. to 35° C., and records 33.9° C., 34° C., 34° C., 34° C., 34° C., 34° C., 34° C., 34° C., 34° C., and 33.5° C.; and the second wearable device determines that 32° C., 30° C., 29° C., 25° C., and 12° C. are outside the range of 33° C. to 35° C., and sets 32° C., 30° C., 29° C., 25° C., and 12° C. as invalid temperatures.

The wearable device establishes a wireless communication connection to the control center in a wireless communication manner, and the wireless communication manner includes but is not limited to Wi-Fi®, ZigBee® (wireless data transmission network platform), Ultra Wideband (UWB, carrier-free communications technology), Bluetooth®, or the like.

When the user goes indoors wearing the wearable device, the wearable device detects a WiFi signal sent out by a home router. In a case with preset registration and pairing, the wearable device may establish a network connection to the home router, and in addition, the home router sends a registration list to the control center, where the registration list includes an identifier of the registered and paired wearable device; the control center receives the registration list sent by the home router, and receives a body temperature that is of the user and that is sent by the wearable devices in the registration list.

Further, when the user wears the wearable device, the wearable device first determines whether the user correctly uses the wearable device.

The first wearable device determines whether the first wearable device is inside the body of the user and is in an operating state; if the first wearable device is inside the body of the user and is in the operating state, the first wearable device determines that the user correctly uses the first wearable device; or if the first wearable device is not inside the body of the user and/or is not in the operating state, the first wearable device determines that the user does not correctly use the first wearable device.

Similarly, the second wearable device determines whether the second wearable device is attached on the skin surface of the user and is in an operating state; if the second wearable device is attached on the skin surface of the user and is in the operating state, the second wearable device determines that the user correctly uses the second wearable device; or if the second wearable device is not attached on the skin surface of the user and/or is not in the operating state, the second wearable device determines that the user does not correctly use the second wearable device.

For example, the first wearable device is a wired earphone, and the wired earphone determines whether the wired earphone is inside an ear of the user and whether a cable connected to the wired earphone is inserted into a mobile terminal. If the wired earphone is inside an ear of the user, and the cable connected to the wired earphone is inserted into a mobile phone, it is determined that the user correctly uses the wired earphone; or if the wired earphone is not inside an ear of the user, and/or the cable connected to the wired earphone is not inserted into a mobile phone, it is determined that the user does not correctly use the wired earphone.

For another example, the first wearable device is a wireless earphone, and the wireless earphone determines whether the wireless earphone is inside an ear of the user and whether the wireless earphone establishes a wireless connection to a mobile terminal. If the wireless earphone is inside an ear of the user, and establishes a wireless connection to a mobile terminal, it is determined that the user correctly uses the wireless earphone; or if the wireless earphone is not inside an ear of the user, and/or does not establish a wireless connection to a mobile terminal, it is determined that the user does not correctly use the wireless earphone.

The mobile terminal may be a mobile phone, a tablet computer, or the like.

Further, a home device with a temperature collection module and a wireless communications module collects status data indoors, and the status data includes a temperature, humidity, illuminance, and the like. The home device sends the status data to a control center.

Step 302: The control center receives the body temperature of the user sent by the wearable device.

In this embodiment of the present disclosure, one control center may be set for one range, or one control center may be set for multiple ranges.

If one control center is set for one range, the control center within the range first obtains a location of the wearable device, and determines, according to the location of the wearable device, whether the wearable device falls within the range. If the wearable device falls within the range, the control center receives the body temperature of the user sent by the wearable device; or if the wearable device does not fall within the range, the process ends.

If one control center is set for multiple ranges, the control center first obtains a location of the wearable device, determines, according to the location of the wearable device, a range including the wearable device, receives the body temperature of the user sent by the wearable device, and controls a temperature of the range including the wearable device.

It should be noted that in this embodiment of the present disclosure, a wearable device outside a range may be set to control a temperature of the range. For example, when a user goes to a parking lot, the user enables a first wearable device and a second wearable device, where the first wearable device measures an in vivo temperature of the user, and sends the in vivo temperature of the user to a control center; and the second wearable device measures a skin temperature of the user, and sends the skin temperature of the user to the control center. The control center receives the in vivo temperature of the user sent by the first wearable device and the skin temperature of the user sent by the second wearable device, and controls an indoor temperature according to the in vivo temperature and skin temperature of the user, so that the indoor temperature is adjusted to be suitable for the user when the user enters the indoor.

Further, in this step, the control center receives the status data sent by the home device.

Step 303: The control center obtains a control parameter of the temperature regulating device according to the body temperature of the user.

If the body temperature of the user includes only the in vivo temperature of the user, step 303 may be implemented by performing the following steps (1) and (2).

(1) The control center determines, according to the in vivo temperature of the user, a first temperature range including the in vivo temperature of the user.

The control center pre-stores a temperature range, and determines, according to the in vivo temperature of the user and the temperature range, the first temperature range including the in vivo temperature of the user.

(2) The control center obtains the control parameter of the temperature regulating device from a correspondence between an in vivo temperature range and a control parameter according to the first temperature range.

The control center pre-stores the correspondence between an in vivo temperature range and a control parameter, and obtains, from the correspondence between an in vivo temperature range and a control parameter, the control parameter that is of the temperature regulating device and that is corresponding to the first temperature range.

The control parameter may include a temperature, humidity, a blowing volume, and the like. The temperature regulating device may be an air conditioner, an electric fan, or the like.

If the body temperature of the user includes the in vivo temperature and the skin temperature of the user, step 303 may be implemented in the following first manner or second manner. In terms of the first implementation manner, step 303 may be implemented by performing the following steps (A) to (C).

(A) The control center determines, according to the in vivo temperature of the user, a first temperature range including the in vivo temperature of the user.

The control center pre-stores an in vivo temperature range, and determines, according to the in vivo temperature of the user, the first temperature range including the body temperature of the user.

(B) The control center determines, according to the skin temperature of the user, a second temperature range including the skin temperature of the user.

The control center pre-stores a skin temperature range, and determines, according to the skin temperature of the user and the skin temperature range, the second temperature range including the skin temperature of the user.

(C) The control center obtains the control parameter of the temperature regulating device from a correspondence among an in vivo temperature range, a skin temperature range and a control parameter according to the first temperature range and the second temperature range.

The control center pre-stores the correspondence among an in vivo temperature range, a skin temperature range and a control parameter, and obtains, from the correspondence among an in vivo temperature range, a skin temperature range and a control parameter, the control parameters that are of the temperature regulating device and corresponding to the first temperature range and the second temperature range.

In terms of the second implementation manner, step 303 may be implemented by performing the following steps (a) to (c).

(a) The control center calculates a temperature parameter of the user according to the in vivo temperature and the skin temperature of the user.

Step (a) may be implemented by performing the following steps (a-1) to (a-2).

(a-1) The control center obtains a first weight corresponding to the in vivo temperature and a second weight corresponding to the skin temperature.

The control center receives the first weight and the second weight that are inputted by the user and that are respectively corresponding to the in vivo temperature and the skin temperature, and stores a correspondence between an in vivo temperature identifier and the first weight, and a correspondence between a skin temperature identifier and the second weight.

In this step, the control center obtains the first weight from the correspondence between the in vivo temperature identifier and the first weight according to the in vivo temperature identifier, and obtains the second weight from the correspondence between the skin temperature identifier and the second weight according to the skin temperature identifier.

Figure 4:
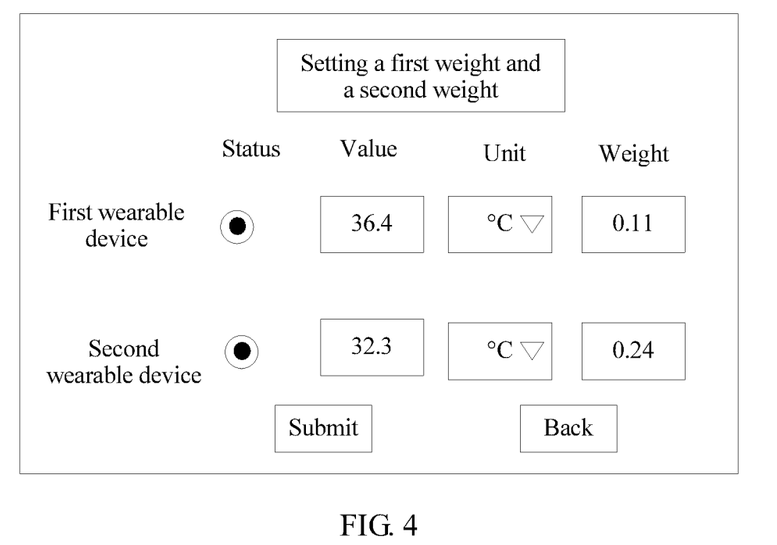
FIG. 4 is an interface diagram of setting a first weight and a second weight according to Embodiment 3 of the present disclosure.

In this embodiment of the present disclosure, an interface for setting the first weight and the second weight is displayed on the control center, and the user may set the first weight and the second weight on the setting interface, as shown in FIG. 4.

(a-2) The control center calculates the temperature parameter of the user according to the in vivo temperature of the user and the first weight, and the skin temperature of the user and the second weight.

The control center calculates a product of the in vivo temperature of the user and the first weight to obtain a first value, calculates a product of the skin temperature of the user and the second weight to obtain a second value, and calculates a sum of the first value and the second value to obtain the temperature parameter of the user.

The control center calculates the temperature parameter of the user every a third preset time according to the method in step (a-2); the third preset time is less than the first preset time and the third preset time is less than the second preset time; and the third preset time may be set and changed according to a demand.

(b) The control center determines, according to the temperature parameter of the user, a third temperature range including the temperature parameter of the user.

The control center pre-stores a temperature parameter range, and determines, according to the temperature parameter of the user and the temperature parameter range, the third temperature range including the temperature parameter of the user.

(c) The control center obtains the control parameter of the temperature regulating device from a correspondence between a temperature parameter range and a control parameter according to the third temperature range.

The control center pre-stores the correspondence between a temperature parameter range and a control parameter, and obtains, from the correspondence between a temperature parameter range and a control parameter, the control parameter that is of the temperature regulating device and that is corresponding to the third temperature range.

Further, the control center obtains the control parameter of the temperature regulating device according to the status data sent by the home device.

Step 304: The control center sends the control parameter to the temperature regulating device.

If one control center is set for multiple rooms, after obtaining the control parameter, the control center sends the control parameter to a temperature regulating device in a room where the wearable device is located.

Further, during a single control period, the control center determines a quantity of currently valid temperatures according to the in vivo temperature sent by the first wearable device and the skin temperature sent by the second wearable device. During this period, if both of the in vivo temperature and skin temperature of the user are invalid temperatures, it is determined that a current control mode is a common control mode, and the control center sends "NA" and a default control parameter to the temperature regulating device; or if only the in vivo temperature of the user is valid, or only the skin temperature of the user is valid, it is determined that the current control mode is an intelligent control mode, and the control center sends "S" and an obtained control parameter to the temperature regulating device; or if both of the in vivo temperature and skin temperature of the user are valid, it is determined that the current control mode is an intelligent control mode, and the control center sends "D" and obtained control parameters to the temperature regulating device.

Step 305: The temperature regulating device receives the control parameter sent by the control center, and regulates an indoor temperature according to the control parameter.

The temperature regulating device receives the control parameter sent by the control center, and starts timing. Before a timing time exceeds a fourth preset time, if a quantity of times with a same control parameter reaches a preset quantity of times, the indoor temperature is regulated during a fifth preset time according to the control parameter; or if the quantity of times with a same control parameter does not reach the preset quantity of times, the indoor temperature is regulated according to a default parameter.

The fourth preset time may be set and changed according to a demand, for example, the fourth preset time is 40 seconds; the preset quantity of times may be set and changed according to a demand, for example, the preset quantity of times is 5; and the fifth preset time may also be set and changed according to a demand, for example, the fifth preset time is 20 minutes.

For example, the control center sends control parameters every 5 seconds. Control parameters sent during a first period are a temperature control target 27° C., and a ventilation volume 20%; control parameters of a second period are a temperature control target 27° C., and a ventilation volume 20%; control parameters of a third period are a temperature control target 27° C., and a ventilation volume 20%; control parameters of the fourth period are a temperature control target 27° C., and a ventilation volume 20%; control parameters of the fifth period are a temperature control target 27° C., and a ventilation volume 20%; control parameters of the sixth period are a temperature control target 27° C., and a ventilation volume 20%; control parameters of the seventh period are a temperature control target 28° C., and a ventilation volume 30%; and control parameters of the eighth period are a temperature control target 29° C., and a ventilation volume 28%. During 40 seconds, a quantity of times with the control parameters, namely, the temperature control target 27° C. and the ventilation volume 20%, is 6, which exceeds 5. Therefore, the temperature regulating device regulates the indoor temperature according to the temperature control target 27° C. and the ventilation volume 20%.

Further, if the temperature regulating device does not receive the control parameter sent by the control center, the temperature regulating device obtains a default parameter, and regulates an indoor temperature according to the default parameter.

Further, in this embodiment of the present disclosure, the control center may further obtain application data, where the application data includes content such as a weather forecast, a work calendar, and a human body metabolism rate; calculate a current control parameter of the temperature regulating device according to the application data with reference to a temperature control model, and send the control parameter to the temperature regulating device, so that the temperature regulating device controls an indoor temperature according to the control parameter, thereby improving a comfort level in an indoor environment.

In this embodiment of the present disclosure, a control center receives a body temperature of a user sent by a wearable device, obtains a control parameter of a temperature regulating device according to the body temperature of the user, and controls the temperature regulating device according to the control parameter. This not only can provide the user with a comfortable indoor environment, but also can improve energy utilization.

Embodiment 4

Figure 5:
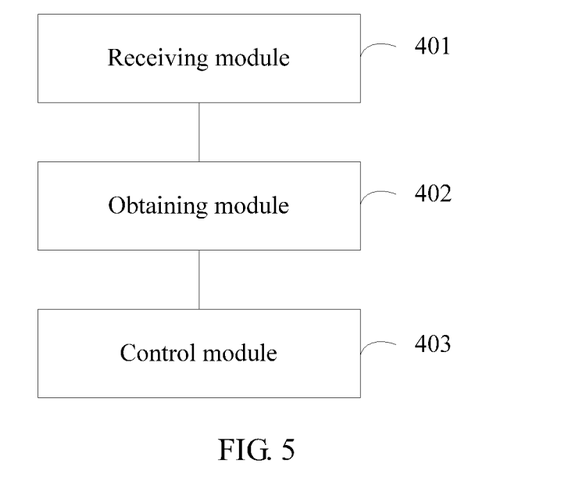
FIG. 5 is a schematic structural diagram of an apparatus for controlling a temperature regulating device according to Embodiment 4 of the present disclosure.

This embodiment of the present disclosure provides an apparatus for controlling a temperature regulating device. Referring to FIG. 5, the apparatus includes a receiving module 401, configured to receive a body temperature of a user sent by a wearable device, and the body temperature of the user includes at least an in vivo temperature of the user; an obtaining module 402, configured to obtain a control parameter of the temperature regulating device according to the body temperature of the user; and a control module 403, configured to control the temperature regulating device according to the control parameter.

Preferably, the obtaining module 402 includes a first determining unit, configured to determine, according to the in vivo temperature of the user, a first temperature range including the in vivo temperature of the user; a first obtaining unit, configured to obtain the control parameter of the temperature regulating device from a correspondence between an in vivo temperature range and a control parameter according to the first temperature range.

Preferably, the body of the user further includes a skin temperature of the user, the wearable device includes a first wearable device and a second wearable device, where the first wearable device is configured to measure the in vivo temperature of the user, and the second wearable device is configured to measure the skin temperature of the user; and the receiving module 401 is configured to: receive the in vivo temperature of the user sent by the first wearable device, and receive the skin temperature of the user sent by the second wearable device.

Preferably, the obtaining module 402 includes a second determining unit, configured to determine, according to the in vivo temperature of the user, a first temperature range including the in vivo temperature of the user; a third determining unit, configured to determine, according to the skin temperature of the user, a second temperature range including the skin temperature of the user; and a second obtaining unit, configured to obtain the control parameter of the temperature regulating device from a correspondence among an in vivo temperature range, a skin temperature range and a control parameter according to the first temperature range and the second temperature range.

Preferably, the obtaining module 402 includes a calculation unit, configured to calculate a temperature parameter of the user according to the in vivo temperature and the skin temperature of the user; a fourth determining unit, configured to determine, according to the temperature parameter of the user, a third temperature range including the temperature parameter of the user; and a third obtaining unit, configured to obtain the control parameter of the temperature regulating device from a correspondence between a temperature parameter range and a control parameter according to the third temperature range.

Preferably, the calculation unit includes an obtaining subunit, configured to obtain a first weight corresponding to the in vivo temperature and a second weight corresponding to the skin temperature; and a calculation subunit, configured to calculate the temperature parameter of the user according to the in vivo temperature of the user and the first weight, and the skin temperature of the user and the second weight.

Preferably, the control module 403 is configured to send the control parameter to the temperature regulating device, so that the temperature regulating device adjusts a temperature according to the control parameter.

In this embodiment of the present disclosure, a control center receives a body temperature of a user sent by a wearable device, obtains a control parameter of a temperature regulating device according to the body temperature of the user, and controls the temperature regulating device according to the control parameter. This not only can provide the user with a comfortable indoor environment, but also can improve energy utilization.

Embodiment 5

Figure 6:
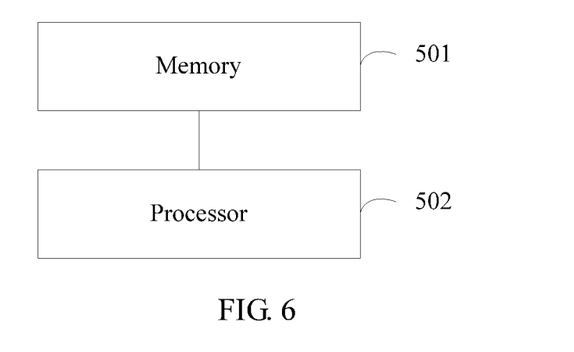
FIG. 6 is a schematic structural diagram of an apparatus for controlling a temperature regulating device according to Embodiment 5 of the present disclosure.

This embodiment of the present disclosure provides an apparatus for controlling a temperature regulating device. Referring to FIG. 6, the base station includes a memory 501 and a processor 502, configured to execute the following method for controlling a temperature regulating device receiving a body temperature of a user sent by a wearable device, where the body temperature of the user includes at least an in vivo temperature of the user; obtaining a control parameter of the temperature regulating device according to the body temperature of the user; and controlling the temperature regulating device according to the control parameter.

Preferably, the obtaining a control parameter of the temperature regulating device according to the body temperature of the user includes determining, according to the in vivo temperature of the user, a first temperature range including the in vivo temperature of the user; and obtaining the control parameter of the temperature regulating device from a correspondence between an in vivo temperature range and a control parameter according to the first temperature range.

Preferably, the body of the user further includes a skin temperature of the user, the wearable device includes a first wearable device and a second wearable device, the first wearable device is configured to measure the in vivo temperature of the user, and the second wearable device is configured to measure the skin temperature of the user; and the receiving a body temperature of a user sent by a wearable device includes receiving the in vivo temperature of the user sent by the first wearable device, and receiving the skin temperature of the user sent by the second wearable device.

Preferably, the obtaining a control parameter of the temperature regulating device according to the body temperature of the user includes determining, according to the in vivo temperature of the user, a first temperature range including the in vivo temperature of the user; determining, according to the skin temperature of the user, a second temperature range including the skin temperature of the user; and obtaining the control parameter of the temperature regulating device from a correspondence among an in vivo temperature range, a skin temperature range and a control parameter according to the first temperature range and the second temperature range.

Preferably, the obtaining a control parameter of the temperature regulating device according to the body temperature of the user includes calculating a temperature parameter of the user according to the in vivo temperature and the skin temperature of the user; determining, according to the temperature parameter of the user, a third temperature range including the temperature parameter of the user; and obtaining the control parameter of the temperature regulating device from a correspondence between a temperature parameter range and a control parameter according to the third temperature range.

Preferably, the calculating a temperature parameter of the user according to the in vivo temperature and the skin temperature of the user includes obtaining a first weight corresponding to the in vivo temperature and a second weight corresponding to the skin temperature; and calculating the temperature parameter of the user according to the in vivo temperature of the user and the first weight, and the skin temperature of the user and the second weight.

Preferably, the controlling the temperature regulating device according to the control parameter includes sending the control parameter to the temperature regulating device, so that the temperature regulating device adjusts a temperature according to the control parameter.

In this embodiment of the present disclosure, a control center receives a body temperature of a user sent by a wearable device, obtains a control parameter of a temperature regulating device according to the body temperature of the user, and controls the temperature regulating device according to the control parameter. This not only can provide the user with a comfortable indoor environment, but also can improve energy utilization.

It should be noted that when the apparatus that is provided in the foregoing embodiment and for controlling a temperature regulating device controls the temperature regulating device, division of the foregoing function modules is merely used as an example for illustration. In actual application, the foregoing functions may be allocated to different function modules and implemented according to a requirement, that is, an inner structure of the apparatus is divided into different function modules to implement all or a part of the functions described above. In addition, the apparatus that is provided in the foregoing embodiment and for controlling a temperature regulating device and the method for controlling a temperature regulating device pertain to a same concept. For a specific implementation process, reference may be made to the method embodiments, and details are not described herein.

A person of ordinary skill in the art may understand that all or some of the steps of the embodiments may be implemented by hardware or a program instructing related hardware. The program may be stored in a computer-readable storage medium. The storage medium may include: a read-only memory, a magnetic disk, or an optical disc.

The foregoing descriptions are merely example embodiments of the present disclosure, but are not intended to limit the present disclosure. Any modification, equivalent replacement, and improvement made without departing from the spirit and principle of the present disclosure shall fall within the protection scope of the present disclosure.

What is claimed is:

1. A method for controlling a temperature regulating device, comprising:
   receiving, from a wearable system comprising a first wearable device and a second wearable device, a body temperature of a user, wherein the body temperature of the user comprises an in vivo temperature of the user and a skin temperature of the user, and wherein receiving the body temperature of the user comprises:
   receiving the in vivo temperature of the user from the first wearable device; and
   receiving the skin temperature of the user from the second wearable device;
   determining, according to pre-stored in vivo temperature ranges, a first temperature range of the pre-stored in vivo temperature ranges, wherein the first temperature range corresponds to the in vivo temperature of the user;
   obtaining, according to a pre-stored correspondence between a respective one of the pre-stored in vivo temperature ranges and a respective one of control parameters of the temperature regulating device, a first control parameter of the temperature regulating device comprising:
   determining, according to the skin temperature of the user, a second temperature range comprising the skin temperature of the user; and
   obtaining the first control parameter from a correspondence between an in vivo temperature range, a skin temperature range and a second control parameter associated with the first temperature range and the second temperature range; and
   controlling the temperature regulating device according to the first control parameter.

2. The method of claim 1, wherein obtaining the first control parameter of the temperature regulating device comprises:
   calculating a temperature parameter of the user according to the in vivo temperature of the user and the skin temperature of the user;
   determining, according to the temperature parameter of the user, a third temperature range comprising the temperature parameter of the user; and
   obtaining the first control parameter of the temperature regulating device from a correspondence between the third temperature parameter range and the second control parameter associated with the third temperature range.

3. The method of claim 1, wherein the method comprises:
   obtaining a first weight corresponding to the in vivo temperature and a second weight corresponding to the skin temperature; and
   calculating a temperature parameter of the user according to the in vivo temperature of the user, the first weight, the skin temperature, and the second weight.

4. The method of claim 1, wherein controlling the temperature regulating device according to the first control parameter comprises sending the first control parameter to the temperature regulating device such that the temperature regulating device adjusts a temperature according to the first control parameter.

5. A wearable device comprising:
a body of the wearable device;
a temperature collection module coupled to the body of the wearable device and configured to collect an in vivo temperature of a user and a skin temperature of the user; and
a wireless communications module coupled to the temperature collection module, wherein the wireless communications module is configured to receive a first control parameter of the temperature regulating device, wherein the first control parameter is related to a pre-stored correspondence between a respective one of a pre-stored in vivo temperature ranges and a respective one of control parameters of a temperature regulating device, wherein the wireless communications module receives the first control parameter according to a first temperature range comprising the in vivo temperature of the user, a second temperature range comprising the skin temperature of the user, and a correspondence between an in vivo temperature range, a skin temperature range and a second control parameter associated with the first temperature range and the second temperature range, and wherein the first control parameter is used to control the temperature regulating device.

6. The wearable device of claim 5, wherein the body of the wearable device is inside the user, wherein the temperature collection module is configured as a temperature sensor, wherein the temperature sensor is configured to collect the in vivo temperature of the user, and wherein the wireless communications module is configured to send the in vivo temperature of the user to a control center.

7. The wearable device of claim 6, further comprising a processor, wherein the processor is configured to:
determine whether the in vivo temperature of the user falls within a preset range;
record the in vivo temperature of the user when the in vivo temperature of the user falls within the preset range; and
mark the in vivo temperature of the user as an invalid temperature when the in vivo temperature of the user is not within the preset range.

8. The wearable device of claim 5, wherein the body of the wearable device is attached on a skin surface of the user, wherein the temperature collection module is configured as a temperature sensor, wherein the temperature sensor is configured to collect the skin temperature of the user, and wherein the wireless communications module is configured to send the skin temperature of the user to a control center.

9. The wearable device of claim 8, further comprising a processor, wherein the processor is configured to:
determine whether the skin temperature of the user falls within a preset range;
record the skin temperature of the user when the skin temperature of the user is within the preset range; and
mark the skin temperature of the user as an invalid temperature when the skin temperature of the user is not within the preset range.

10. An apparatus for controlling a temperature regulating device, comprising:
a memory;
a processor coupled to the memory; and
a receiver coupled to the processor and the memory, wherein the receiver is configured to receive a body temperature of a user from a wearable device comprising a first wearable device and a second wearable device, wherein the body temperature of the user comprises an in vivo temperature of the user and a skin temperature of the user, wherein the receiver is configured to receive the in vivo temperature of the user from the first wearable device and is configured to receive the skin temperature of the user from the second wearable device, and wherein the processor is configured to:
determine, according to a pre-stored in vivo temperature ranges, a first temperature range of the pre-stored in vivo temperature ranges, wherein the first temperature range corresponds to the in vivo temperature of the user;
obtain, according to a pre-stored correspondence between a respective one of the pre-stored in vivo temperature ranges and a respective one of control parameters of the temperature regulating device, a first control parameter of the temperature regulating device, wherein the first control parameter is obtained according to:
determining, according to the in vivo temperature of the user, a first temperature range comprising the in vivo temperature of the user;
determining, according to the skin temperature of the user, a second temperature range comprising the skin temperature of the user; and
obtaining the first control parameter from a correspondence between an in vivo temperature range, a skin temperature range and a second control parameter associated with the first temperature range and the second temperature range; and
control the temperature regulating device according to the first control parameter.

11. The apparatus of claim 10, wherein the processor is further configured to:
calculate a temperature parameter of the user according to the in vivo temperature and the skin temperature of the user;
determine, according to the temperature parameter of the user, a third temperature range comprising the temperature parameter of the user; and
obtain the first control parameter of the temperature regulating device from a correspondence between the third temperature parameter range and the second control parameter associated with the third temperature range.

12. The apparatus of claim 10, wherein the processor is further configured to:
obtain a first weight corresponding to the in vivo temperature and a second weight corresponding to the skin temperature; and
calculate a temperature parameter of the user according to the in vivo temperature of the user and the first weight, and the skin temperature of the user and the second weight.

13. The apparatus of claim 10, wherein the processor is further configured to send the first control parameter to the temperature regulating device.

* * * * *